(12) United States Patent
Waag et al.

(10) Patent No.: US 10,201,054 B2
(45) Date of Patent: Feb. 5, 2019

(54) OPTICAL DETECTION DEVICE, ITS METHOD FOR OPERATING AND COMPUTER PROGRAM

(71) Applicants: Technische Universitaet Braunschweig, Braunschweig (DE); Universitat de Barcelona, Barcelona (ES)

(72) Inventors: Andreas Waag, Wuerzburg (DE); Juan Daniel Prades Garcia, Barcelona (ES); Martin Hoffmann, Bruehl (DE)

(73) Assignees: TECHNISCHE UNIVERSITAET BRAUNSCHWEIG, Braunschweig (DE); UNIVERSITAT DE BARCELONA CENTRE DE PATENTS DE LA UB, Barcelona (ES)

( * ) Notice: Subject to any disclaimer, the term of this patent is extended or adjusted under 35 U.S.C. 154(b) by 0 days.

(21) Appl. No.: 15/741,852

(22) PCT Filed: Jul. 6, 2016

(86) PCT No.: PCT/EP2016/065977
§ 371 (c)(1),
(2) Date: Jan. 4, 2018

(87) PCT Pub. No.: WO2017/005792
PCT Pub. Date: Jan. 12, 2017

(65) Prior Publication Data
US 2018/0199409 A1 Jul. 12, 2018

(30) Foreign Application Priority Data
Jul. 7, 2015 (EP) .................................... 15175671

(51) Int. Cl.
*H05B 33/08* (2006.01)
*G02B 21/00* (2006.01)
(Continued)

(52) U.S. Cl.
CPC ......... *H05B 33/0851* (2013.01); *G02B 21/00* (2013.01); *H01L 33/08* (2013.01); *G02B 21/06* (2013.01)

(58) Field of Classification Search
CPC ...................................................... G02B 21/06
(Continued)

(56) References Cited

U.S. PATENT DOCUMENTS 8,624,968 B1 1/2014 Hersee et al.
9,835,839 B2 * 12/2017 Hein ...................... G02B 21/06
(Continued)

FOREIGN PATENT DOCUMENTS

EP 1 794 811 B1 6/2011
EP 2 665 100 A2 11/2013
WO 2014/053415 A1 4/2014

OTHER PUBLICATIONS

Zuo et al.; "Lensless phase microscopy and diffraction tomography with multi-angle and multi-wavelength illuminations using a LED matrix"; Optics Express, vol. 23, No. 11, May 22, 2015, pp. 14314-14328.

*Primary Examiner* — Thuy Vinh Tran
(74) *Attorney, Agent, or Firm* — W&C IP

(57) ABSTRACT

The invention relates to a light emitting device comprising a light source array which comprises a plurality of separately electrically controllable electric light sources which are arranged in a matrix structure or any other defined geometrical arrangement. Advantageously, the pixel pitch of the light source array is less than (500) nanometer. The invention further relates to an optical detection device comprising a light detection device, which is arranged for producing an electrical signal in response to light reaching a light detection side of the light detection device, and to a method for operating such an optical detection device. The invention
(Continued)

Figure 1:
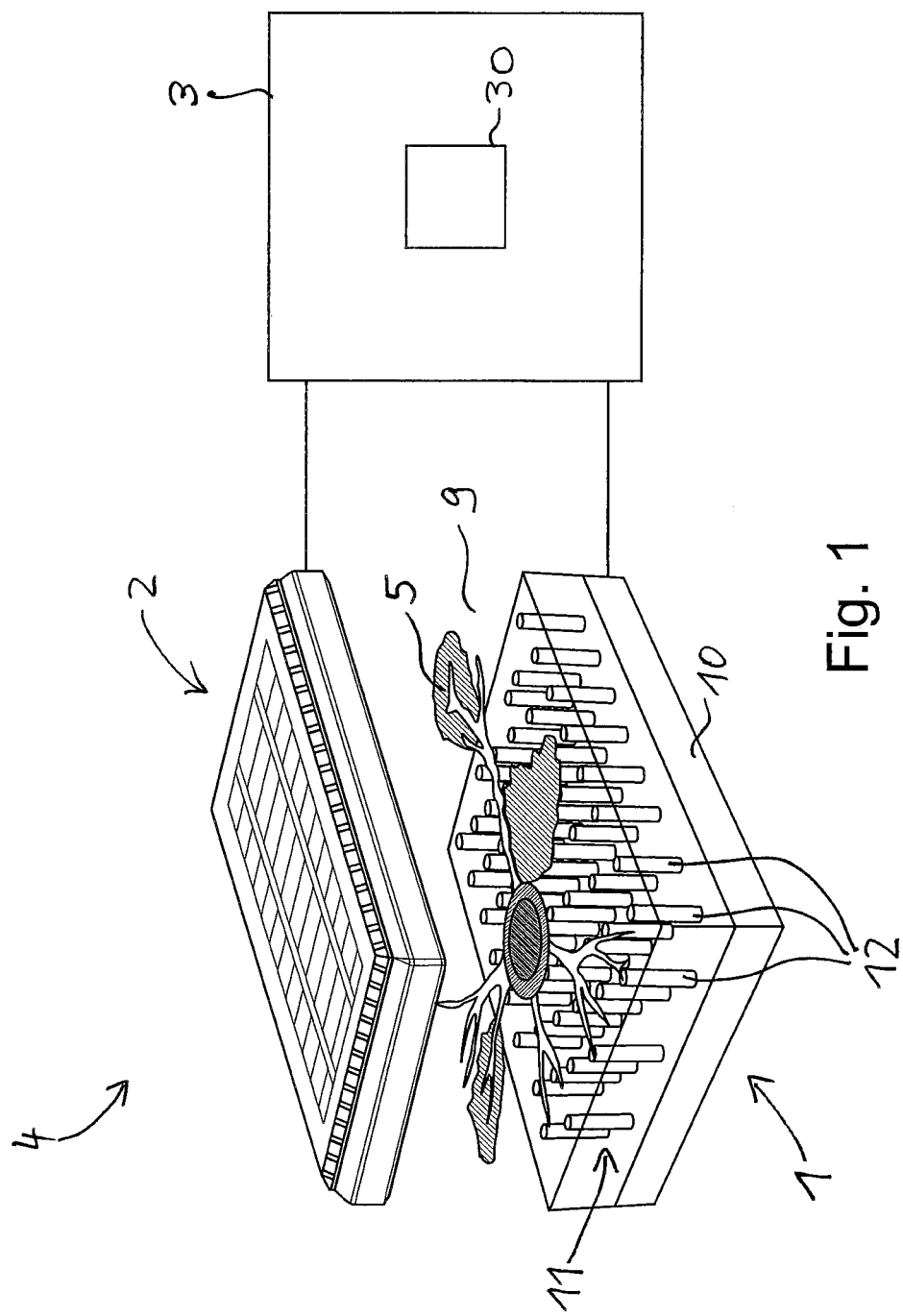

further relates to a computer program with program coding means arranged for performing such a method.

13 Claims, 5 Drawing Sheets

(51) Int. Cl.
*H01L 33/08* (2010.01)
*G02B 21/06* (2006.01)

(58) Field of Classification Search
USPC .......................................... 356/904; 359/385
See application file for complete search history.

(56) References Cited

U.S. PATENT DOCUMENTS

2004/0157354 A1   8/2004   Kuriyama et al.
2015/0029583 A1*  1/2015   Hein ..................... G02B 5/045
                                                      359/390

\* cited by examiner

OPTICAL DETECTION DEVICE, ITS METHOD FOR OPERATING AND COMPUTER PROGRAM

The invention relates to a light emitting device comprising a light source array, which comprises a plurality of separately electrically controllable electrical light sources, which are arranged e.g. in a matrix structure or any other defined geometrical arrangement. The invention further relates to an optical detection device comprising a light detection device, which is arranged for producing an electrical signal in response to light reaching a light detection side of the light detection device, and to a method for operating such an optical detection device. The invention further relates to a computer program with program coding means arranged for performing such a method.

Light emitting devices of the aforementioned type are known e.g. in the form of display units of laptop computers, tablets and smartphones. Optical detection devices of the above-mentioned type are known e.g. in the form of optical microscopes like confocal microscopes, e.g. disclosed in WO 2014/053415 A1. In such optical systems, which use light e.g. in the visible spectral range, the spatial resolution is limited by the physical laws of diffraction. For some applications it is desired to observe very small structures with a higher resolution, e.g. single proteins, DNA-molecules or the development of internal cellular macromolecular complexes and structures with optical microscopes. Attempts to overcome the physical resolution limit have led to the so called super resolution techniques like STED, STORM or PALM, which rely on particular non-linear optical properties of the object under investigation or on other very complex optical environments.

It is an object of the present invention to provide for devices which allow "normal" (diffraction-limited) optical resolution optical and also super resolution with less complicated optical systems. Further, advantageous methods for achieving super resolution with less complex optical systems are an object of the invention. Further, an advantageous computer program with program coding means arranged for performing such a method is an object of the invention.

These objects of the invention are achieved by any of claims 1, 8 and 13. In contrast to proposals in the prior art, the present invention can achieve optical super resolution by a completely different approach, namely by implementing spatially highly resolved illumination instead of spatially highly resolved light detection. Of course, the present invention can also be combined with spatially highly resolved light detection, but this is not an absolute requirement. For keeping the technical efforts and costs of the inventive devices low, it is advantageous to concentrate on spatially highly resolved illumination instead of spatially highly resolved light detection.

According to the invention a light emitting device is proposed comprising a light source array which comprises a plurality of separately electrically controllable electric light sources which are arranged in a matrix structure or any other defined geometrical arrangement. Therefore, the single electric light sources can be activated by applying an electrical signal to the light source. Advantageously, the pixel pitch of the light source array is less than 500 nanometer. In further advantageous embodiments of the invention, the pixel pitch can be less than 200 nanometer, or less than 100 nanometer. In this way, a super resolution illumination device is proposed which can form the basis of a super resolution optical detection device with low technical complexity and superior robustness. In this way, each of the electric light sources forms one pixel of the matrix structure. The pixel pitch in such a structure is defined as the distance between the center of light emission of one electric light source and the center of the light emission of the next (neighbouring) electric light source.

The light emitting device makes it possible to achieve super resolution capabilities without additional optical elements, like lenses, optical lattices or similar optical elements. This has the advantage that the physical limits of such elements like the diffraction limit can be avoided.

Such a pixel pitch provides for an optical resolution of the light emitting device which is far below the optical limits of a human viewer. Therefore, such small pixel pitch would not be required for computer displays and similar applications, but can be used for implementing a super resolution optical detection device, as further explained hereinafter, or for other technical applications which can be improved by such super resolution illumination equipment. For example, the light emitting device of the invention can be used as an illumination tool for photolithography, e.g. in the area of illuminating photosensitive material of electronic printed circuit boards, or for 3D printing applications.

The light emitting device can be implemented with any suitable technology, like liquid crystal display (LCD) technology. According to an advantageous embodiment of the invention, the light sources of the light source array are light emission diodes (LEDs). This has the advantage that the light emitting device can be produced using available nanoscale production methods. Another advantage is that by such LEDs the light emitting device is capable of emitting light with a high intensity with moderate electrical power consumption, compared to other technologies. Another advantage is that such light sources can be electrically controlled in a very fast manner without significant activation and deactivation delays.

The LEDs can be of any type. It is particularly advantageous to implement the LEDs in form of galliumnitride-based light emission diodes.

Generally, the light sources of the light source array can be established in an at least partially overlapping manner, e.g. by implementing LED-structures within a semiconductor chip. In such case, the diameter of a light source can be larger than the pixel pitch.

According to an advantageous embodiment of the invention, the diameter of each light source of the light source array is less than 500 nanometer. In particular, the diameter of each light source can be smaller than the pixel pitch. In this way, the light sources do not overlap, but are separated from each other. This further improves the super resolution capabilities of the light emitting device and an optical detection device comprising such light emitting device.

In an advantageous embodiment, the electric light sources are arranged for emitting light from a light emission side of the light source array. The light emission side can be a planar surface of the light source array or a non-planar surface. In an advantageous embodiment of the invention, the light source array comprises at least 1000×1000 pixels (1000× 1000 separately electrically controllable electric light sources). However, the more pixels/light sources are implemented in the light source array, the better results are achieved in terms of image size. The size of the light emission side of the light source array should be large enough for the desired applications, e.g. for illuminating objects to be examined with an optical detection device comprising the light emitting device. For example, the size of the light emission side may be one or more square centimeters.

Light emitting devices with such dimensions of the electrical light sources can be produced by so called nanotechnologies. For example, it is possible to produce arrays of nano-LEDs in which the dimension of the single LEDs is 50 nanometer or below. In such a structure each nano-LED is directly addressable.

According to an advantageous embodiment of the invention, the light sources of the light source array are arranged for emission of light in the visible spectral range, in particular within the wavelength range from 360 to 600 nanometer. Further, the light sources can be arranged for emission of light in the wavelength range from 400 to 550 nanometer. This allows the emission of visible light and therefore the implementation within an optical detection device using visible light.

An optical detection device according to the invention comprises a light detection device, which is arranged for producing an electrical signal in response to light reaching a light detection side of the light detection device, wherein the optical detection device comprises a light emitting device comprising a light source array which comprises a plurality of separately electrically controllable electric light sources which are arranged in a matrix structure or any other defined geometrical arrangement. The pixel pitch of the light source array maybe less than 500 nanometer. Further, a light emission side of the light source array is arranged opposite of the light detection side of the light detection device, such that light emitted from one or more light sources of the light source array can be detected by the light detection device, wherein the light emission side of the light source array is spaced away from the light detection side of the light detection device, forming an intermediate space between them for positioning an object to be examined with the optical detection device. With such an optical detection device the aforementioned advantages can be achieved, in particular the super resolution capabilities for optical examination of objects positioned in the intermediate space.

In particular, no optical elements like lenses are required to be located in the light path from the light emission side of the light source array and the light detection side of the light detection device.

In this way, the optical detection device can be realised in the form of a super resolution optical detection device. This means that the optical detection device has a resolution which is below the diffraction limit of light in the spectral range emitted by the light source array.

According to an advantageous embodiment of the invention the light detection device is coupled with the light emitting device via a control device which is arranged for controlling the several light sources according to a defined activation scheme for an integrated, synchronized processing of the data received from the light detection device. In such way the super resolution capabilities of the light emitting device can be advantageously utilized, thus creating a super resolution image result based on the light signals received by the light detection device.

According to an advantageous embodiment of the invention the light detection device comprises one or more single light sensor elements, the number of light sensor elements being less than the number of light sources of the light source array. In other words, a light detection device with less resolution capabilities can be used, compared to the light emitting device. The number of light sources in the light source array can be significantly higher than the number of light sensor elements, e.g. by a factor of 100 or 1000 or more. Therefore, simple and cheap elements for constituting the light detection device can be used. For example, the light detection device can be one photosensitive element, like a photodiode, a photoresistor or a phototransistor. The light detection device can be a CMOS chip. The light detection device can have a very high sensitivity, e.g. with single photon detection capability. Another advantageous embodiment comprises a light detection device in the form of a digital camera chip, e.g. in the form of a CCD chip. The optical detection device, in particular the light detection device, can be realised without optical elements like lenses, lattices and so on.

For example, the light detection device can comprise a plurality of single light sensor elements which are arranged in a matrix structure, forming an optical sensor array. In such case, an image of an object positioned in front of an optical capturing surface of the optical sensor array can be captured by the optical sensor elements, the image comprising a plurality of pixels.

However, a resulting image of an object positioned in the intermediate space can be calculated based on the specific lighting pattern of the electric light sources of the light source array, thereby reaching a spatial resolution which is defined by the light source array and not by the optical detection device.

The light sensitive area of the light detection device or the optical capturing surface can be smaller than the dimensions of the light emission side of the light source array. According to an advantageous embodiment of the invention the light emission side of the light source array is fully covered by the light detection side, or the optical capturing surface, of the light detection device. This has the advantage that the light detection device can directly receive the vertically emitted light beams from the light sources. In such way, any measuring deviations or inaccuracies through inclined light beams can be avoided.

The invention is further related to a method for operating an optical detection device of the aforementioned type. The method is applicable to an optical detection device having a light emitting device with lower resolution as discussed before, namely with a pixel pitch not less than 500 nanometer However, it is advantageous when the optical detection device comprises a light emitting device of the aforementioned type having the high resolution pixel pitch of the light source array which is less than 500 nanometer. The method is characterized by:

a) separately or groupwise activating some of the light sources of the light source array according to a defined activation scheme for emitting light, like sequentially or according to defined patterns, b) receiving emitted light directly from the activated light sources or resulting light therefrom by the light detection device, c) capturing the electrical signals produced by the light detection device in response to light reaching the light detection side of the light detection device and/or storing the electrical signals or data representative thereof with a reference to the defined activation scheme of the light sources, d) producing an at least two dimensional image representation of an object positioned in the intermediate space of the optical detection device from the captured and/or stored signals and/or data.

This allows to accomplish the common inventive concept of the present invention, namely the simplicity of the device without using optical elements. It is a further common inventive concept of the present invention to accomplish super resolution by a spatially highly resolved illumination rather than by spatially highly resolved light detection can be achieved. As a result, the aforementioned advantages can be achieved. The image representation of the object can be e.g. a digital pixel image.

Since each of the light sources can be controlled with a high repetition rate, a structured excitation of the light sources and an imaging of the received light can be explicitly fast, in particular in real time. It is possible to achieve a repetition rate better than 100 frames per second.

According to an advantageous embodiment of the invention, the resolution of the produced image representation is higher than the resolution of the light detection device and/or the same or similar to the resolution of the light source array. In particular, the produced image representation can have a resolution of 500 nanometer or better, which means less than 500 nanometer. In particular, the resolution can be 200 nanometer or less, or 100 nanometer or less.

According to an advantageous embodiment of the invention, the temporal behaviour of the electrical signals produced by the light detection device in response to light reaching the light detection side of the light detection device is captured and/or stored or data representative thereof, wherein the image representation is produced using the temporal behaviour which was captured and/or stored. Based on such evaluation of the temporal behaviour of the received light additional analysis results of the examination of the object in the intermediate space can be gained. For example, the temporal decay of the light signal after switching a light source off can give additional information about the object in the intermediate space.

Further, the light detection device can be sensitive to the colour of light which is received. An evaluation of the colour of light can give additional information about the object in the intermediate space.

According to an advantageous embodiment of the invention, a shadow image of an object positioned in the intermediate space is captured and evaluated. Such an evaluation can give additional information about the object in the intermediate space.

According to a further advantageous embodiment, a near field shadow image and/or structured light shadow image, based upon a structured activation of light sources of the light source array, can be captured and evaluated. In this sense, structured light means the activation of a certain pattern of light sources. Such an evaluation can give additional information about the object in the intermediate space.

According to an advantageous embodiment of the invention, the fluorescent capabilities of an object positioned in the intermediate space are captured and evaluated. Such an evaluation can give additional information about the object in the intermediate space.

According to an advantageous embodiment of the invention at least some of the light sources of the light source array are activated in a pulsed manner with a defined pulsing frequency. In this way, additional information about the object in the intermediate space can be gained.

By using the pulsed activation of light sources further information can be included within the light transmitted from the light source to the light detection device. This can be done by amplitude modulation, frequency modulation and/or phase modulation of the pulsed activation of the light sources.

In addition, the light detection device can be able to discriminate different wavelengths (like is the case in a conventional CCD chip), which will give further information on the object under test. The wavelength sensitivity can be realised even by two or more different light detectors located next to each other, since according to the present invention they do not have to be at the exact same position in space in order to get the same image of the object under test.

By such means the quality of signal detection as well as the amount of information on the receiving side can be improved. In particular, any signal noise can be reduced. In this way, it is also possible to filter out any disturbing ambient light influences.

The invention is further related to a computer program with program coding means arranged for performing one or more of the aforementioned methods, if the computer program is executed on a computer. The computer can be a part of the aforementioned control device.

The invention is now further described by examples using the attached drawings. The drawings show in FIG. 1 an optical detection device in a perspective view and FIG. 2 the optical detection device in a side view and FIGS. 3 to 5 methods of operation of the optical detection device.

In the drawings same elements are marked with same numerals.

Figure 2:
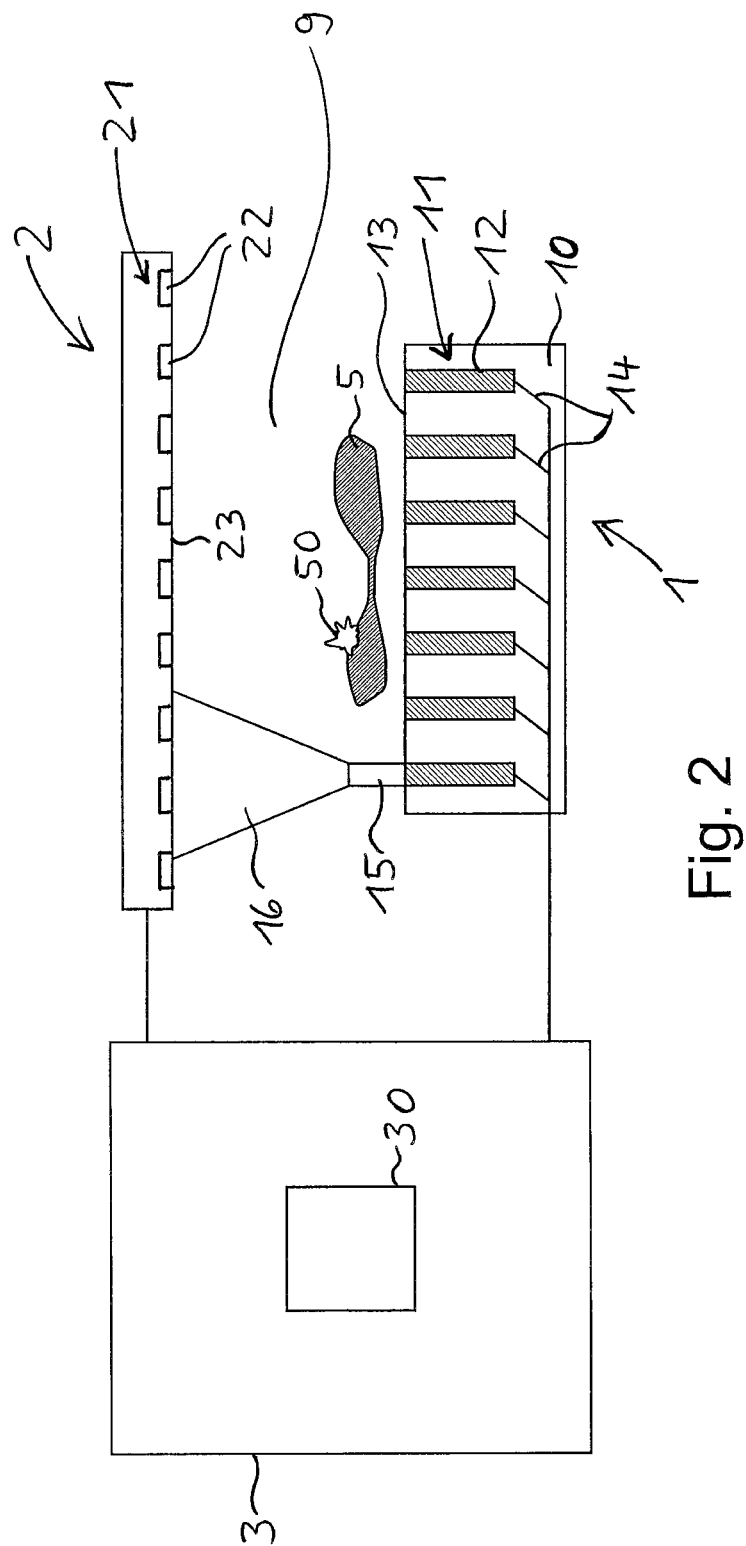

The optical detection device 4 shown in FIGS. 1 and 2 comprises a light emitting device 1, a light detection device 2 and a control device 3. The optical detection device 4 is hereinafter also called "SuperLight". The light emitting device 1 is hereinafter also called "SuperLight engine".

The light emitting device 1 comprises a light source array 11 which comprises a plurality of electric light sources 12 in the form of nanoLEDs. The nanoLEDs 12 are formed in a semiconductor material based on a substrate 10. The light source array is hereinafter also called "nanoLED array". The nanoLEDs 12 can be separately addressed, which means that they are separately electrically controllable, via control lines 14. The control lines 14 are directly or indirectly, e.g. in the form of a databus, connected with the control device 3.

The light detection device 2 comprises a plurality of light sensor elements 22 which form a light detection array 21. The light detection device 2 is electrically connected with the control device 3. The light detection device is hereinafter also called "photodetector".

The control device 3 comprises a microprocessor 30 and other elements of a microprocessing computing device, like memory, interfaces, etc. The control device 3 comprises a control programme which executes control methods, like the method explained before. In this way, the nanoLEDs 12 are activated and deactivated and the resulting light is received by the light detection device 2. The resulting signals are fed from the light detection device 2 to the control device 3.

The control device 3 can control on- and off-status of the nanoLEDs 12, including intensity as a function of time, of each nanoLEDs separately or groups of nanoLEDs.

As can be seen in FIG. 2, near field light 15 and far field light 16 is emitted from a light emission side 13 of the nanoLED array 11. The light is received on a light detection side 23 through the light sensor elements 22 of the light detection device 2. Between the light emission side 13 and the light detection side 23 some space is foreseen, forming an intermediate space 9 for positioning an object 5 to be examined with the SuperLight 4. For example, the object 5 can be a biological structure to which a marker 50, e.g. in the form of a fluorescent label, has been added.

The basic principle of SuperLight 4 is shown in FIGS. 1 and 2. An array 11 of nanoLEDs 12 (pitch <50 nm) is combined with a separate photodetector 2. The object 5 (e.g. biological object like a nerve cell, or a nanostructure) is located on top of the nanoLED array 11. The nanoLEDs 12 can be switched independently on and off, one after the other, in full synchronization with a broad area, single pixel, photodetector 2. The typical footprint of an array 11 is e.g. 0.1-1 mm$^2$, the typical distance to the photodetector 2 is e.g. 0.1-1 mm. The nanoLED array 11 will enable the user to switch on and off one single nanoLED 12 after another, at high repetition speed. As a consequence, the photodetector 2 sequentially measures signals that originate from different well known locations in space in each time slot. The signal measured at the photodetector 2 will integrate the amount of light transmitted through the object 5 in each position. In this way, the "shadow" image of the object 5 can be reconstructed from the time domain signal. Contrary to conventional microscopy, spatial resolution is provided by the illumination source, and not by the photodetector 2 or the optical system. As a result, there is no need for any additional complex optical system, since large area integrating photodetectors can be used. As a result, high throughput semiconductor technology can make such novel microscopic devices ubiquitously available in our daily life. Like a CCD camera in a mobile phone takes images from the macroscopic world, the SuperLight chip "camera" can take images from the nanoscale world of bio- and medical environments.

Figure 3:
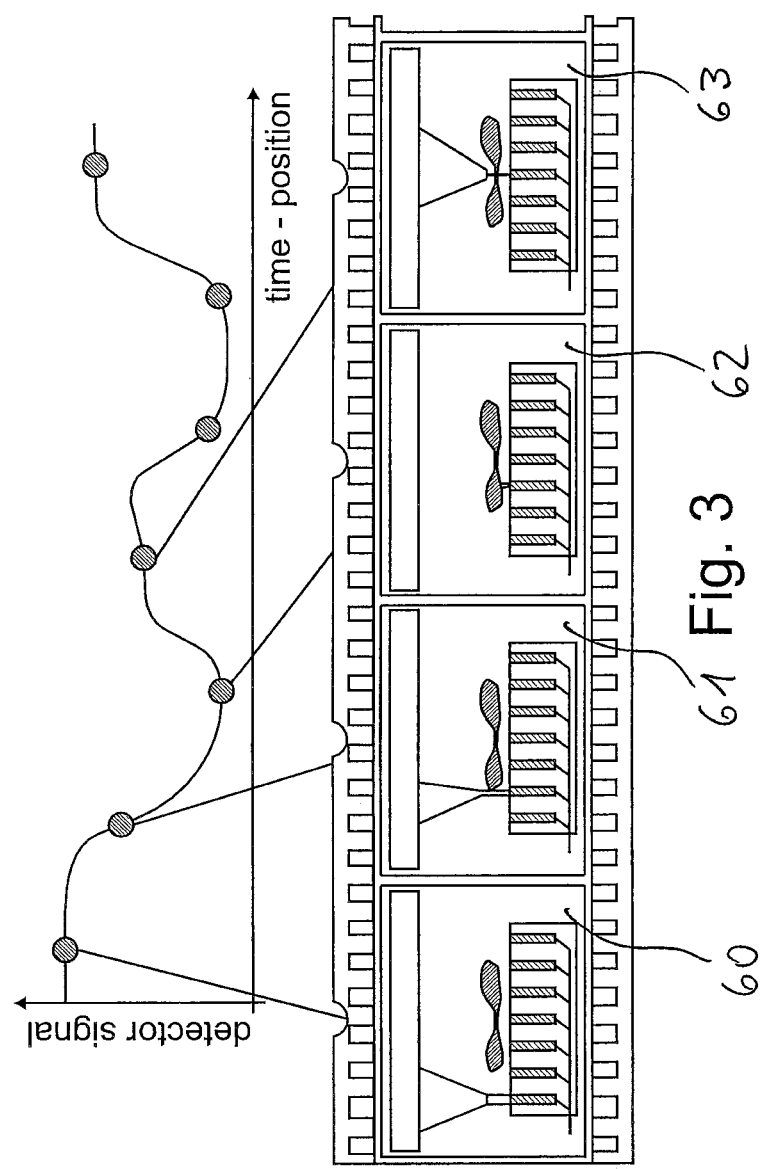
Figure 4:
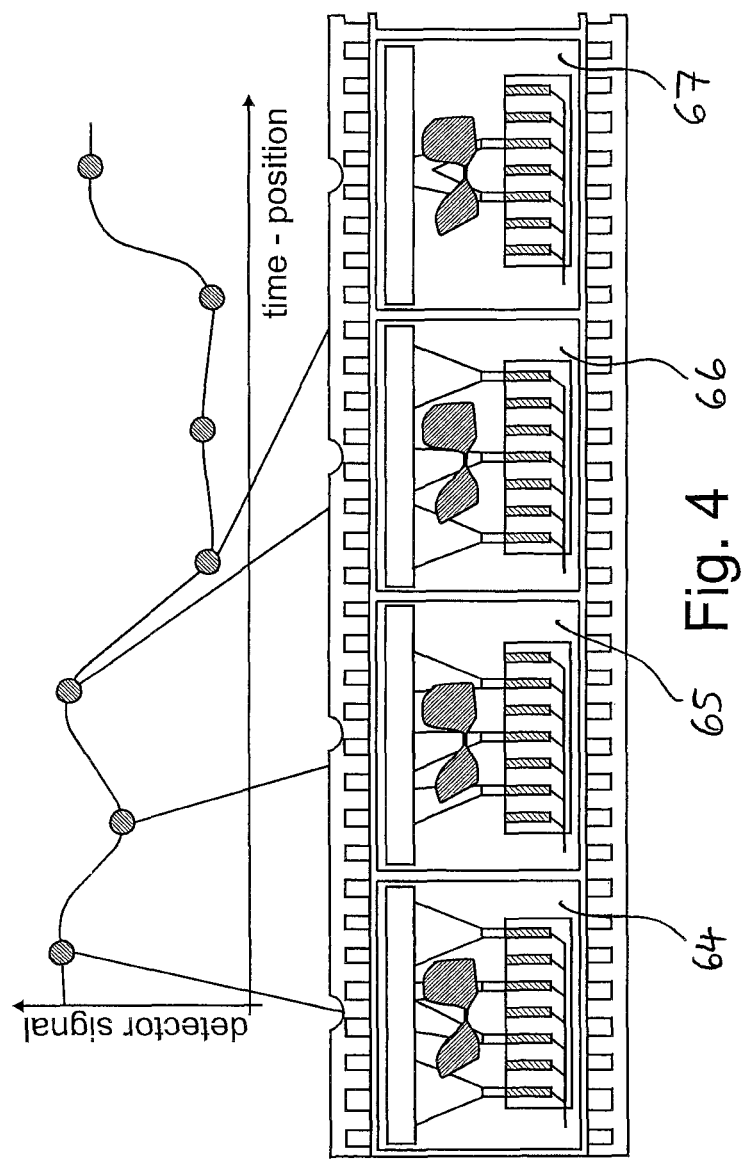

In FIGS. 3 and 4 direct imaging modes are shown. In a first operating mode shown in FIG. 3, light-sample interactions should occur under near-field conditions, in which light blocking takes place in the subdiffraction regime directly on top of the light emitting surface. Under these conditions, spatial resolution will solely be limited by the distance between two neighbouring nanoLEDs 12. Targeting a pitch below 50 nm, the spatial resolution will be substantially lower than given by the optical diffraction limit. In more generalised far field situations (thick samples, at larger distances or with a complex internal structure) the possibility to operate each nanoLED 12 individually also enables structured illumination approaches. This is, illuminating the sample with predefined light patterns to gain both spatial resolution and insight into the third dimension, at the nanoscale. All this leads to a "shadow microscopy imaging" mode based on low-spatial-resolution photodetection of the direct illumination patterns that emerge after "scanning" the sample with nanoLEDs 12 at different positions.

As can be seen in FIG. 3, the nanoLEDs 12 are activated one after the other. In time step 60, the leftmost nanoLED 12 is activated. The light is not blocked by the object 5 and therefore reaches the photodetector 2. In time step 61, the next nanoLED 12 is activated. Its light is partially obstructed by the object 5. In time steps 62, a further nanoLED 12 is activated whose light is completely obstructed by the object 5. In time step 63, another nanoLEDs 12 is activated whose light is partly absorbed by the object 5.

While FIG. 3 shows in the curves the results of the detector signal of a thin object 5 under test, leading to a near-field shadow image, in FIG. 4 the curve shows the structured light shadow image in a situation where the object 5 is a thicker sample.

As can be seen in FIG. 4, in this operating mode more than one nanoLED 12 is activated, creating a light pattern. The pattern of light can be changed, as can be seen in the time steps 64, 65, 66 and 67. This creates different images on the photodetector 2 with complex information on the real geometry and optical property of the object 5 under test.

In near field conditions, the sample 5 directly masks the emission of the nanoLED 12 obtaining a transmitted light signal (in time) that can be converted into a shadow image (in space). If light-sample interaction occurs in far-field conditions, structured light sequences (involving ensembles of nanoLEDs 12) can be used to extract structural information after image processing.

Figure 5:
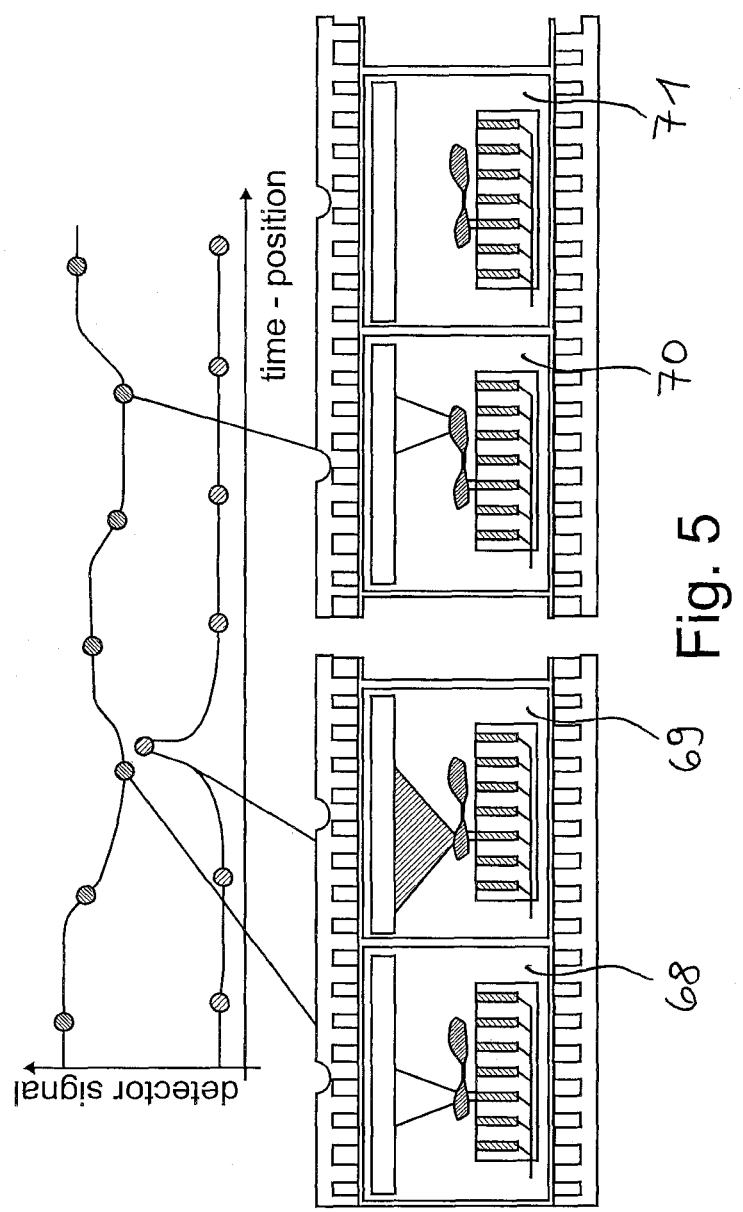

FIG. 5 shows a simultaneous imaging/analysis mode. Due to the high time resolution of both nanoLEDs 12 and photodetector 2, the emitter-detector system can also be used to image fluorescent-dye labelled processes. This operating mode is shown in FIG. 5. In a single nanoLED 12 spot, marker 50 will be excited. The photodetector 2 will have single photon sensitivity and will be able to detect fluorescence after the nanoLED pulse is switched off again (time-gated mode). The fluorescence decay can be measured and analysed, opening the door to discriminate different fluorescent sources with different time decay (i.e. target analytes) emerging from one single spot, simultaneously. Also nanoLEDs 12 with different wavelengths or filter layers directly applied on top of the nanoLEDs 12 or photodetector 2 surface will enable wavelength sensitive excitation and/or emission.

Evidently, all these operating modes could be combined to operate simultaneously, just by properly sequencing the nanoLED activation and deactivation with the photodetection modes and measurement time. Such combinations enable many measurement strategies with unprecedented resolution, analytical power and real time imaging capabilities. Remarkably, all these possibilities solely rely on the combination of nanoLED arrays 11 closely integrated with a broad area photodetector 2, without the necessity of employing complex optical systems for imaging. The whole system will finally be put onto a single chip.

The nanoLEDs 12 can be produced with GaN technology, which enables tuning the wavelength of emitted light by means of bandgap engineering and/or in combination with optical dyes or phosphorous emitters (from UV to IR). Nanolithography (nanoimprint) makes it feasible to reach ananoLED 12 to nanoLED 12 distance of less than 50 nm.

The different modes of operation of the SuperLight (direct shadow imaging, fluorescence imaging, etc.) will require dealing with a wide range of light intensities in the detection stage, from high intensity to single photon. At the same time, the most advanced applications will require fast detection and fast processing times. To cope with all these requirements, a CMOS multimode photodetector 2 is used. This may include a linear photodiode mode to deal with bright applications, and a single photon avalanche photodiode mode, for single photon counting. In order to accommodate the control electronics (i.e. different photodetector modes, nanoLED driving and synchronization, etc.) these photodetectors may be produced in CMOS technology. Image processing enables extracting information from the SuperLight images, which is not directly visible, by unfolding scattering and diffraction, and analysing the results from structured light illumination patterns.

The photodetector 2 may be established using a single photon CMOS process, permitting the integration of the required control and processing electronics in one chip, leading to a compact SuperLight device. This is advantageous for achieving tight synchronization and timing constraints. The photodetector 2 itself may be an Avalanche Photodiode which will be operated in linear or avalanche (Geiger) mode, depending on the application. The linear mode can be used for obtaining high multiplication gains that allow determining the number of incident photons with great precision in direct illumination imaging. In Geiger mode we can achieve single photon sensitivities to address single molecule detection and secondary emission imaging. In order to extend the analytical power of the Superlight 4, a fluorescence lifetime imaging mode (FLIM) can be added, to acquire the decay of fluorescence signals, facilitating the discrimination between direct emissions and secondary signals.

For an effective low signal-to-noise photodetector 2, an area of 1.5×1.5 μm can be used. These may serve as base units, being replicated into large area photodetectors. Even at highest resolution and maximum sensitivity one could estimate a maximum array size of approximately 900 pixels for one fundamental base unit on the chip, leading to minimum frame rates of 10-100 frames/s. This base unit can be used as a building block, which can be repeated to cover arbitrarily large areas, without losing performance.

To integrate the CMOS chip and the nanoLED array 11 into a single package, a silicon structure embedding both chips face to face may be used. Such structure, based on Multi-Chip Modules (MCM) and Micromechanic Manufacturing Technology (MMT), can satisfy high performance goals.

Now, a few out of the numerous novel applications will be addressed in order to demonstrate the potential of the SuperLight:

Metrology at the Nanoscale:

This includes the broad metrological characterisation of the SuperLight nanoLED array light engines. At the same time, the potential of using the nanoLED arrays 11 as standards for nanoscale calibration experiments (intensity and length calibration standard) may be addressed. DNA origami structures may serve as well defined nano-objects under investigation.

To quantify the spatial resolution of the SuperLight device with light-source limited resolution novel calibration standards are adopted, produced by the DNA origami technique. The idea behind DNA origami is to fold a long (7,000-9,000 nucleotides (nt)) single-stranded DNA (ssDNA), called a scaffold strand, together with short (~20-50 nt) oligonucleotides (also called staple strands) into a pre-defined structure. The position of each staple strand in the fully folded nanostructure is known; therefore objects such as fluorescent dyes can be positioned with a well defined spatial resolution of a nanometer over a length scale of up to 1 μm. These nanorulers maybe immobilized directly on the nanoLED 12 array and imaged. Measuring samples with varying distances between the marks will directly yield the quantitative spatial resolution of the SuperLight chip. Structures of higher complexity may include artificial filaments with very high persistence lengths in the micrometer range and natural filaments such as acting close to the basal membrane of fixed cells. Wavelengths down-converters employing fluorescence resonance energy transfer (FRET) on DNA origami are used, which enable detection at a wavelength far away from the GaN excitation wavelengths.

Real-Time Imaging of Living Tissues:

SuperLight enables for the first time the investigation in living samples of sequentially unfolding modular pathologies that center in cell to cell interfaces. The SuperLight technology allows the integration of morphological data with molecular measurements on living material without the need for destructive sample preparation. A microfluidic expansion to the SuperLight chip may be constructed for in-vitro research on primary lung fibroblasts or other biologic structures.

In general, SuperLight could serve to observe intracellular processes in general. For example, SuperLight can be used for in-vitro imaging of inter- and intracellular processes in an application for the analysis of the underlying mechanisms of Chronic Obstructive Pulmonary Disease (COPD). Already identified functional mRNA markers involved in the molecular mechanisms leading to COPD are suggesting a sequentially unfolding modular pathology that centers on the failure of surface cell integrity. However, these results are gained through molecular analysis, as so far it is not possible to view these events in living tissues. It becomes possible by using SuperLight measurement compartments by integrating nanoLED 12 arrays and photodetectors 2 into a fully automated microfluidic handling system. The measurement setup can provide both, conventional microscopic techniques for control characterization purposes and the new SuperLight technique, simultaneously.

Light-Induced Surface Phenomena:

The nanoLED arrays 11 may be used for nanofabrication purposes, such as maskless lithography and nanopositioning of organic species at sub-100 nm resolution in order to e.g. implement cost effective multiplex bioassay by optically activating the immobilization of biologic receptors or nucleic acids. This will simplify both the array configuration and readout steps, enabling multiplex assays of unprecedented flexibility and complexity.

Using the SuperLight engine for spatially resolved optical activation of surfaces makes it possible creating arbitrary patterns of surface-activated areas and subsequently confirm the modification of polymer films (for nano-photolithography) and binding of biomolecules (for bioassay formation) at optically defined positions. In addition, the SuperLight engine can be used to measure the fluorescence from the immobilized species (proteins) at the location of the nanoLED 12. The results can be analyzed by comparison with conventional external imaging techniques such as Total Internal Reflection Fluorescence (TIRF) microscopy. For further miniaturization of the illuminated and hence activated area, the combination of optical nanoantennas, such as bowtie antennas, with nanoLEDs 12 is advantageous. This does not only lead to further focusing of the activating light to smaller dimensions, but does also lead to significant fluorescence or Raman enhancement of target molecules bound to these hot-spots. To this end, bowtie antenna arrays may be aligned to the nanoLED chip and nanoLED illumination may enable placing optical emitters and bioassays in the hot-spot of the nanoantennas. This provides for a flexible bioassay based on highly miniaturized multiplex arrays.

Optogenetic Applications:

In cell cultures or hippocampal neurons, light-sensitive modulators of membrane voltage or second messengers as cAMP or Ca2+ are co-expressed with genetically encodable fluorescent proteins that report changes of membrane voltage, Ca2+ or protein expression. Functionality of these cells or networks may be tested using complex illumination patterns (in shape, time and colour). The approach is designed as an innovative optogenetic approach for fast and high resolution analysis of neuronal network communication, going far beyond the capabilities of present state-of-the-art optogenetic experiments.

The application uses structured illumination (by a varying group of nanoLEDs 12 at the same time) of neuronal substructures of cellular compartments for the activation of optogenetic actuators, namely light-activated proteins, and to monitor changes of cellular parameters as membrane voltage of Ca2+distribution with unprecedented precision. The cells can grow directly on the nanoLED array 11, after appropriate surface passivation. In a first application a very general optogenetic procedure is applied, and express in human embryo kidney cell lines (HEK-cells) various optogenetic tools such as Channelrhodopsin and the photoactivated cyclase bPAC, both connected to the marker protein GFP. This makes it possible to grow cells on nanoLED arrays 11 and reconstruct cellular structures from sequential spot illumination. Fluorescence can be recorded as delayed fluorescence, if the life time of the fluorescence is long enough (>1 ns), or, preferentially, fluorescence can be monitored during illumination. For the latter approach wavelength selecting photodiodes with blocked sensitivity below 500 nm are used in the photodetector 2. This makes it possible to coexpress actuators as ChR and genetically encodable Ca2+indicators or voltage sensors as reporters and to monitor light-induced Ca2+ or voltage changes by using different wavelength for activation and monitoring, which needs the complex image processing. As a result, a simple laboratory instrument for everyday use can be constructed that provides super resolution images of subcellular activators and reporters in cellular networks without employing microscopic devices, substantially extending existing possibilities limited today by simple glass fiber based illumination.

The invention claimed is:

1. Optical detection device comprising a light detection device, which is arranged for producing an electrical signal in response to light reaching a light detection side of the light detection device, a light emitting device comprising a light source array which comprises a plurality of separately electrically controllable electric light sources which are arranged in a matrix structure or any other defined geometrical arrangement, a light emission side of the light source array being arranged opposite of the light detection side of the light detection device, such that light emitted from one or more electric light sources of the light source array can be detected by the light detection device, wherein the light emission side of the light source array is spaced away from the light detection side of the light detection device, forming an intermediate space between them for positioning an object to be examined with the optical detection device, characterized in that the light detection device comprises one or more single light sensor elements, the number of the light sensor elements being less than the number of the electric light sources of the light source array.

2. Optical detection device according to claim 1, wherein the light detection device is coupled with the light emitting device via a control device which is arranged for controlling the several electric light sources according to a defined activation scheme and for an integrated, synchronized processing of the data received from the light detection device.

3. Optical detection device according to claim 1, wherein the light emission side of the light source array is fully covered by the light detection side of the light detection device.

4. Optical detection device according to claim 1, wherein a pixel pitch of the light source array is less than 500 nanometer.

5. Optical detection device according to claim 1, wherein the diameter of each electric light source of the light source array is less than 500 nanometer.

6. Optical detection device according to claim 1, wherein the electric light sources of the light source array are arranged for emission of light in a visible spectral range.

7. Optical detection device according to claim 1, wherein the electric light sources of the light source array are light emitting diodes (LEDs).

8. Method for operating an optical detection device comprising:
providing and optical detection device comprising a light detection device which is arranged for producing an electrical signal in response to light reaching a light detection side of the light detection device, a light emitting device comprising a light source array which comprises a plurality of separately electrically controllable electric light sources which are arranged in a matrix structure or any other defined geometrical arrangement, a light emission side of the light source array being arranged opposite of the light detection side of the light detection device, such that light emitted from one or more electric light sources of the light source array can be detected by the light detection device, wherein the light emission side of the light source array is spaced away from the light detection side of the light detection device, forming an intermediate space between them for positioning an object to be examined with the optical detection device, characterized in that the light detection device comprises one or more single light sensor elements, the number of the light sensor elements being less than the number of the electric light sources of the light source array;

separately or groupwise activating some of the electric light sources of the light source array according to a defined activation scheme for emitting light, like sequentially or according to defined patterns, receiving emitted light directly from the activated electric light sources or resulting light therefrom by the light detection device, capturing the electrical signals produced by the light detection device in response to light reaching the light detection side of the light detection device and/or storing the electrical signals or data representative thereof with a reference to the defined activation scheme of the light sources, producing an at least two dimensional image representation of an object positioned in the intermediate space of the optical detection device from the captured and/or stored signals and/or data.

9. Method according to claim 8, wherein the temporal behaviour of the electrical signals produced by the light detection device in response to light reaching the light detection side of the light detection device is captured and/or stored or data representative thereof, wherein the image representation is produced using the temporal behaviour which was captured and/or stored.

10. Method according to claim 8, wherein a shadow image of an object positioned in the intermediate space is captured and evaluated.

11. Method according to claim 8, wherein the fluorescent capabilities of an object positioned in the intermediate space are captured and evaluated.

12. Method according to claim 8, wherein at least some of the electric light sources of the light source array are activated in a pulsed manner with a defined pulsing frequency.

13. A non-transitory storage medium encoded with a computer program executable on a computer to provide instructions for operating an optical device, the instructions comprising:
separately or groupwise activating some of electric light sources of a light source array according to a defined activation scheme for emitting light,
receiving emitted light directly from activated electric light sources or resulting light therefrom by a light detection device,
capturing electrical signals produced by a light detection device in response to light reaching a light detection side of the light detection device and/or storing electrical signals or data representative thereof with a reference to the defined activation scheme of the light sources, producing an at least two dimensional image representation of an object positioned in an intermediate space of the optical detection device from the captured and/or stored electrical signals and/or data, wherein the electric light sources, the light source array, and the light detection device are included in the optical detection device, and wherein the light detection device is arranged for producing an electrical signal in response to light reaching a light detection side of the light detection device, wherein a light emitting device comprising the light source array which comprises a plurality of separately electrically controllable electric light sources which are arranged in a matrix structure or any other defined geometrical arrangement, has a light emission side of the light source array arranged opposite of the light detection side of the light detection device such that light emitted from one or more electric light sources of the light source array can be detected by the light detection device, wherein the light emission side of the light source array is spaced away from the light detection side of the light detection device, forming an intermediate space between them for positioning an object to be examined with the optical detection device, characterized in that the light detection device comprises one or more single light sensor elements, the number of the light sensor elements being less than the number of the electric light sources of the light source array.

* * * * *